United States Patent [19]

Abdullah et al.

[11] Patent Number: 4,544,497
[45] Date of Patent: Oct. 1, 1985

[54] LIQUID CRYSTAL MATERIALS CONTAINING SUBSTITUTED BICYCLO(2,2,2)OCTANES

[75] Inventors: Hilal M. Abdullah, Waziria, Iraq; Jennifer Constant, Powick, England; George W. Gray, Cottingham, England; Damien G. McDonnell, Malvern, England; Kenneth J. Toyne, Hull, England

[73] Assignee: The Secretary of State for Defence in Her Britannic Majesty's Government of the United Kingdom of Great Britain and Northern Ireland, London, England

[21] Appl. No.: 573,716

[22] Filed: Jan. 25, 1984

[30] Foreign Application Priority Data

Jan. 28, 1983 [GB] United Kingdom ............... 8302395

[51] Int. Cl.⁴ ...................... G02F 1/13; C09K 3/34
[52] U.S. Cl. .................... 252/299.5; 252/299.62; 350/350 R; 568/664; 568/665; 585/20; 585/21; 585/22
[58] Field of Search ............ 585/20, 21, 22; 568/664, 665; 252/299.5, 299.62; 350/350 R

[56] References Cited

U.S. PATENT DOCUMENTS

| | | | |
|---|---|---|---|
| 4,118,335 | 10/1978 | Krause et al. | 252/299.5 |
| 4,180,475 | 12/1979 | Schadt et al. | 252/299.5 |
| 4,198,130 | 4/1980 | Boller et al. | 252/299.5 |
| 4,219,256 | 8/1980 | Grat et al. | 252/299.62 |
| 4,419,262 | 12/1983 | Petrzilka | 252/299.61 |
| 4,431,853 | 2/1984 | Sato et al. | 252/299.63 |
| 4,439,015 | 2/1984 | Rich et al. | 252/299.63 |
| 4,464,020 | 8/1984 | Le Berre et al. | 252/299.01 |

FOREIGN PATENT DOCUMENTS

| | | | |
|---|---|---|---|
| 58512 | 8/1982 | European Pat. Off. | 252/299.62 |
| 72204 | 2/1983 | European Pat. Off. | 252/299.62 |
| 2636684 | 2/1978 | Fed. Rep. of Germany | 252/299.5 |
| 56-16582 | 2/1981 | Japan | 252/299.5 |
| 56-36568 | 4/1981 | Japan | 252/299.5 |

OTHER PUBLICATIONS

C.A. 87-38976g, 1977.
C.A. 65-5379g, 1966.
C.A. 95-24347f, 1980.
Gray, G. W., et al., Mol. Cryst. Liq. Cryst., vol. 75, pp. 95-108 (1981).

Primary Examiner—Teddy S. Gron
Attorney, Agent, or Firm—Cushman, Darby & Cushman

[57] ABSTRACT

Liquid crystal compositions are described which comprise a mixture of compounds and which includes at least one additive compound characterized in that the composition includes one or more additive compounds of Formula I as follows:

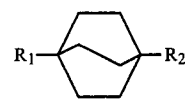

I wherein $R_1$ represents an alkyl group, $R_2$ represents an alkyl or alkoxy group or hydrogen and

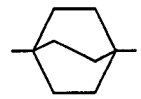

represents a 1,4-disubstituted bicyclo(2,2,2)octane ring. The preparation and properties of novel compounds of Formula I are also described. These liquid crystal compositions are useful in display devices such as digital calculators and word displays.

7 Claims, 7 Drawing Figures

LIQUID CRYSTAL MATERIALS CONTAINING SUBSTITUTED BICYCLO(2,2,2)OCTANES

The present invention relates to liquid crystal materials and additives for use in them.

BACKGROUND OF THE INVENTION

The use of liquid crystal materials to exhibit electro-optical effects in display devices such as digital calculators, watches, meters and simple word displays is now well known. However, known liquid crystal materials are not ideal in all respects and a considerable amount of work is currently being carried out in the art to improve their properties. Liquid crystal materials normally consist of mixtures of compounds; improved materials are obtained by forming new mixtures having an improved combination of properties.

Although liquid crystal materials normally consist mainly of compounds which exhibit a liquid crystal phase by themselves, the materials may contain components which do not exhibit such a phase. Compounds forming such components exhibit a virtual or monotropic liquid crystal to isotropic liquid transition (clearing point) at a temperature below their melting point. As is well known to those skilled in the art, monotropic or virtual transitions may be detected respectively by rapid cooling of the liquid phase or by dissolving the compound in a material exhibiting a liquid crystal phase, observing the change in the transition to the isotropic liquid phase of the material by the addition and calculating the virtual transition temperature by extrapolation of the data from a series of such mixtures of known composition.

Compounds which do not exhibit a liquid crystal phase by themselves are useful as additives to liquid crystal materials, eg to improve the liquid crystal temperature range (ie the range over which the material exhibits a liquid crystal phase) and/or to improve the viscosity of the liquid crystal material.

The liquid crystal temperature range of a material is important because it determines the operating temperature range of the display device. This range is desirably as great as possible.

The viscosity of a liquid crystal material is important because it determines the speed of response of the display device, ie the times required to switch the display from the off state to the on state and vice versa. The viscosity is desirably as low as possible. The viscosity of a mixture of compounds forming a liquid crystal material is determined by the viscosity of the individual compounds.

Strictly speaking, the response times are dependent on a number of viscosity coefficients but the main coefficient to be considered is that known as the "flow aligned" viscosity coefficient (see for example the article entitled "Flow aligned viscosities of Cyanobiphenyls" by J. Constant and E P Raynes Mol. Cryst. Liq. Cryst. (1980) Vol 62 pages 115–124). The term "viscosity" as used in this specification is to be understood to mean the flow aligned coefficient in the nematic liquid crystal phase (mesophase) unless otherwise specified.

Compounds normally incorporated in liquid crystal materials for electro-optical applications may generally be represented in their simplest generalised form by formula A as follows:

$$X-Y-X' \qquad A$$

where X and X' indepedently represent aromatic or alicyclic ring structures and Y represents a simple bridging group such as CO.O or a direct carbon-carbon bond.

Formula A normally applies to such compounds whether or not they exhibit a liquid crystal phase by themselves.

The groups X and X' may for example include a 1,4-disubstituted benzene ring, a trans-1,4-disubstituted cyclohexane ring, or a 1,4-disubstituted bicyclo(2,2,2)octane ring. Known compounds of the type which include a bicyclo(2,2,2)octane ring include known compounds of formulae B and C as follows:

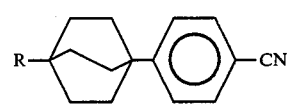

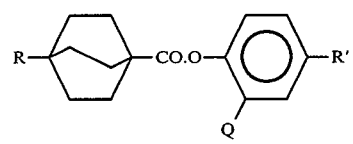

where R and R' are alkyl groups and Q is hydrogen or fluorine. Compounds of formulae B and C are described in published UK Patent Applications Nos. 2027027A and 2063250A for example.

We have now discovered that a class of bicyclo(2,2,2)octane compounds which surprisingly are not of the generalised formula A are useful as additives in liquid crystal materials.

BRIEF DESCRIPTION OF THE INVENTION

According to the present invention in a first aspect there is provided a liquid crystal material which comprises a mixture of compounds and which includes at least one additive compound characterised in that the material includes one or more additive compounds of Formula I as follows:

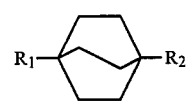

wherein $R_1$ represents an alkyl group, $R_2$ represents an alkyl or alkoxy group or hydrogen and

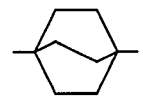

represents a 1,4-disubstituted bicyclo(2,2,2)octane ring. Preferably $R_1$ and $R_2$ each contain not more than twelve carbon atoms.

According to the present invention in a second aspect there is provided a compound of formula I suitable for use in a liquid crystal material wherein $R_1$ is an n-alkyl group having from 3 to 8 carbon atoms inclusive and $R_2$ is an n-alkyl or n-alkoxy group having from 1 to 8 carbon atoms inclusive.

Preferably, $R_2$ in Formula I is n-alkyl having from 3 to 8 carbon atoms.

DETAILED DESCRIPTION OF THE INVENTION

Figure 1:
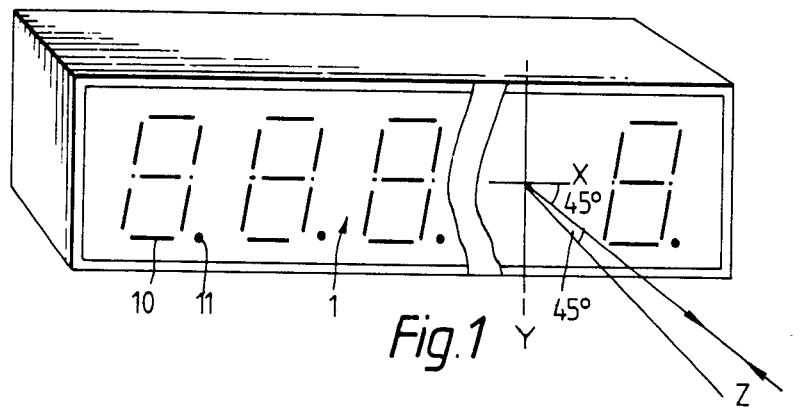
FIG. 1 is a front view of a twisted digital display.
Figure 2:
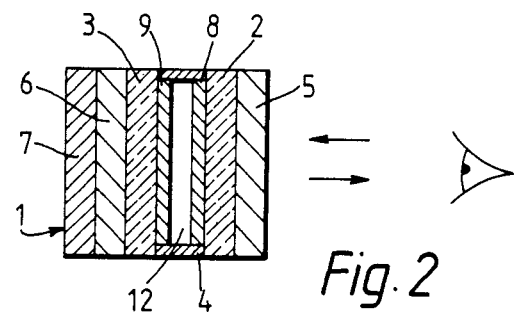
FIG. 2 is a sectional view of the display shown in FIG. 1.

Compounds of Formula I can provide very attractive low viscosity additives to liquid crystal material and may show aspects of superiority compared with known low viscosity additives.

For example, compounds of Formula I can show a similar reduction in viscosity but a smaller depression of clearing point (liquid crystal-to-isotropic liquid transition temperature) than the additives of formula D as follows:

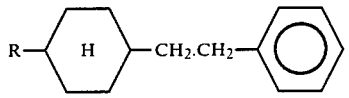

D where R is n-alkyl, when added to the same host liquid crystal material. Compounds of formula D are described in copending UK Patent Application No. GB 2106127A.

The compounds of formula I may be prepared by routes in which the individual procedures are known, the overall routes being new. For example the following routes may be used.

Route 1 ($R_2$ = alkyl)

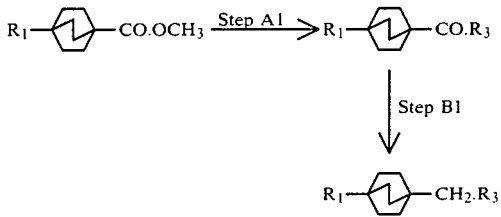

where $CH_2.R_3 = R_2$

Route 2 ($R_2$ = methyl)

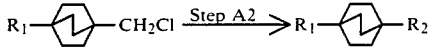

Route 3 ($R_2$ = alkoxy)

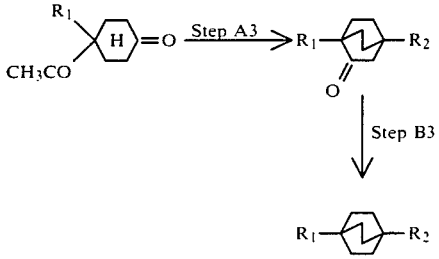

-continued

Route 4 ($R_2$ = hydrogen)

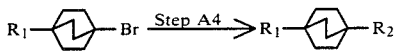

The compounds of Formula (I) have a small dielectric anisotropy (when added to liquid crystal materials) and may be added to liquid crystal materials of positive or negative dielectric anisotropy, known and referred to herein respectively as "positive" or "negative" materials, without significantly affecting the dielectric anisotropy of such materials. As is well known to those skilled in the art the dielectric anisotropy of the liquid crystal material is necessary to give electro-optical operation and its sign (for a given frequency) is chosen according to the kind of electro-optical device in which the material is to be used.

Normally, the liquid crystal material in which the compound of Formula (I) is contained will comprise a host material which comprises one or more liquid crystal compounds having a low melting point (<80° C.) which preferably together with the additive(s) show a liquid crystal phase (preferably nematic or chiral nematic) at room temperature (20° C.) together with one or more additives, eg to reduce viscosity and/or enhance liquid crystal temperature range, the additive(s) including at least one compound of Formula I.

The upper limit of the percentage by weight which the compound(s) of Formula I constitute in the mixture with the host material will depend on the host material but typically the compound(s) will form between 2 and 50% by weight in total, for example between 5 and 30% by weight inclusive in total.

The host material to which the compound(s) of Formula I is added may be one of the following materials:

(i) a positive nematic material for use in twisted nematic effect devices including multiplexed devices; an example of such a device is given below;

(ii) a negative material preferably also with a pleochroic dye, for use in Fréedericksz effect devices (negative nematic type) in which the molecular arrangement may be changed from the homeotropic texture (OFF state) to the homogeneous texture (ON state) by an electric field; an example of such a device is given below;

(iii) a positive nematic material, preferably also with a pleochroic dye for use in Fréedericksz effect devices (positive nematic type) in which the molecular arrangement may be changed from the homogeneous texture (OFF state) to the homeotropic texture (ON state) by an electric field;

(iv) a negative material which is a cholesteric (chiral nematic) of suitable resistivity (about $10^9$ ohm-cm), for use in cholesteric memory mode devices in which the molecular arrangement may be changed from a homogeneous texture (OFF state) to a turbulent scattering focal conic texture (ON state) by an electric field;

(v) a strongly negative material which is a cholesteric, preferably together also with a pleochroic dye, for use in cholesteric-to-nematic phase change effect devices (positive contrast typ) in which the molecular arrangement may be changed from a weakly scattering, ie clear, surface aligned homeotropic texture (OFF state) to a strongly scattering twisted homogeneous texture (ON state) by an electric field;

(vi) a positive material which is a cholesteric, preferably together also with a pleochroic dye, in cholesteric-to-nematic phase change effect devices (negative contrast type) in which the molecular arrangement may be changed from a scattering focal conic texture (OFF state) to a clear homeotropic texture (ON state) by an electric field;

(vii) a negative nematic material of suitable resistivity (about $10^9$ ohm-cm), in dynamic scattering effect devices in which the molecular arrangement may be changed from a clear homeotropic texture (OFF state) to a turbulent scattering texture (ON state) by an electric field;

(viii) a positive nematic material in two frequency switching effect devices (which may be twisted nematic effect devices) in which the dielectric anisotropy of the material may be changed from (at low frequency) positive (OFF state) to negative (ON state) by the application of a high frequency electric field.

The construction and operation of the above devices and the general kinds of material which are suitable for use in them are themselves known.

The host material to which one or more compounds of Formula I are added may itself be a mixture of two or more compounds selected for the particular device application.

Where a host material is for use in a twisted nematic effect, cholesteric to nematic phase change effect (negative contrast type) or Fréedericksz effect (positive nematic type) device the material preferably contains one or more compounds selected from the following families to give a liquid crystal phase at room temperature as well as a positive dielectric anisotropy.

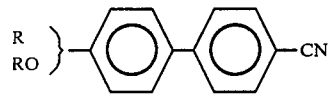

Formula (IIIa)

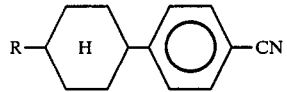

Formula (IIIb)

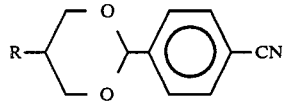

Formula (IIIc)

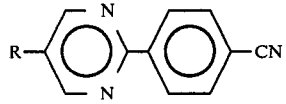

Formula (IIId)

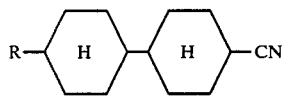

Formula (IIIe)

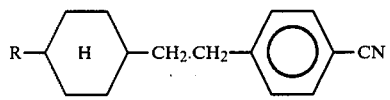

Formula (IIIf)

where the various groups R are the same or different alkyl groups (preferably n-alkyl having up to 10 carbon atoms).

The material may also contain one or more high (>100° C.) clearing point compounds (typically up to about 35% by weight) of the following classes to extend the liquid crystal temperature range of the material at its upper end:

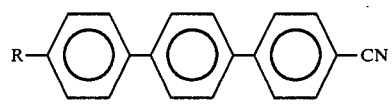

Formula (IVa)

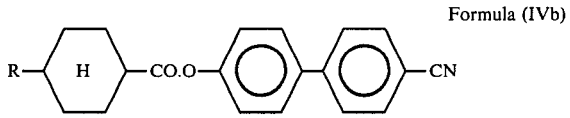

Formula (IVb)

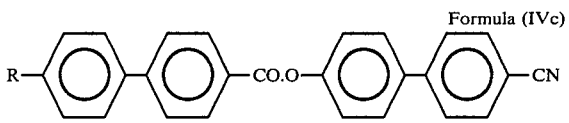

Formula (IVc)

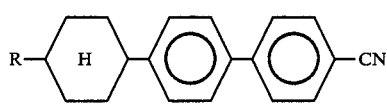

Formula (IVd)

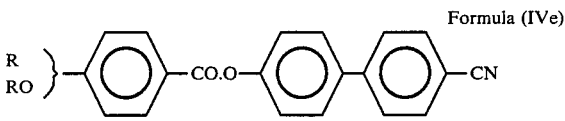

Formula (IVe)

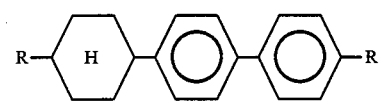

Formula (IVf)

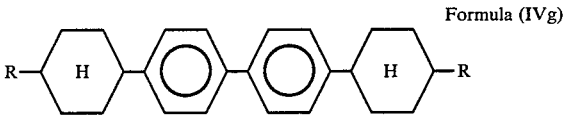

Formula (IVg)

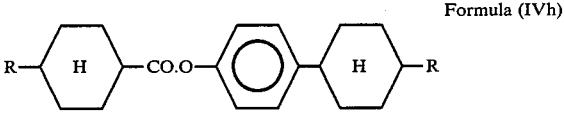

Formula (IVh)

where R is as defined above.

The compounds of Formula I are particularly suitable for use in liquid crystal materials which may be used in multiplexed twisted nematic effect devices. As taught in published UK Patent Application Nos. 2,031,010A and 2,063,287A the multiplexibility of a strongly positive host material, eg consisting of biphenyl compounds of Formula (IIIa) and/or the PCH compounds of Formula (IIIb), together with one or more high clearing point compounds selected from the classes of Formulae (IVa to h), may be improved by the addition of a component of low dielectric anisotropy. This improvement is believed to be brought about by the disruption of anti-parallel pairing of the molecules of the cyano compounds caused by introduction of the material of low dielectric anisotropy.

The component of low dielectric anisotropy may comprise one or more compounds of Formula I optionally together with one or more compounds selected from the following known families:

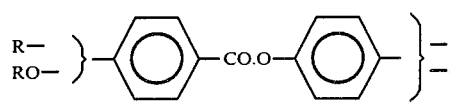
Formula (Va)

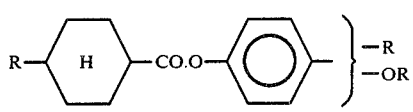
Formula (Vb)

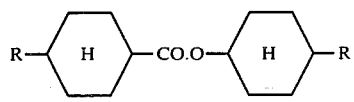
Formula (Vc)

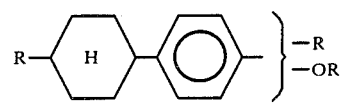
Formula (Vd)

Formula (Ve)

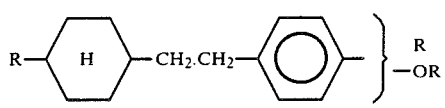
Formula (Vf)

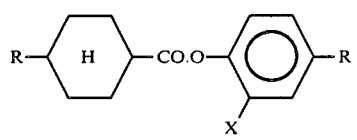
Formula (Vg)

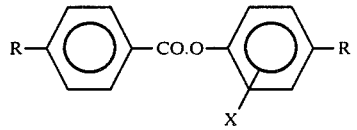
Formula (Vh)

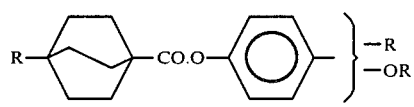
Formula (Vi)

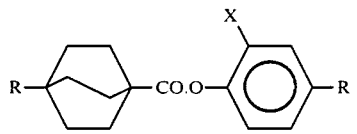
Formula (Vj)

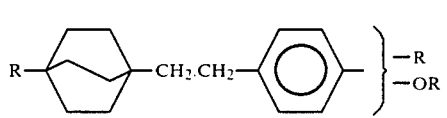
Formula (Vk)

where X = halo, preferably fluoro.

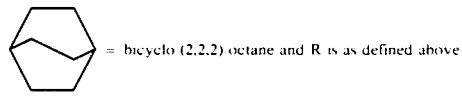 = bicyclo (2,2,2) octane and R is as defined above

A multiplexed twisted nematic device may also contain a small amount, eg up to about 2% by weight, of a chiral additive, eg the BDH compound C 15.

Thus, a liquid crystal material suitable for a multiplexed twisted nematic effect device embodying the present invention preferably comprises the components in Table 1 as follows:

TABLE 1
Liquid crystal material composition for multiplexed twisted nematic operation

| Component | Constituents | Percentage by weight |
|---|---|---|
| Component 1: low melting point positive compound(s) giving a room temperature nematic phase. | One or more compounds selected from Formulae (IIIa) to (IIIf) above. | 5–80%, preferably 40–70% |
| Component 2: high clearing point liquid crystal compounds | One or more compounds selected from Formulae (IVa) to (IVh). | 5–30%, preferably 10–30% |
| Component 3: low dielectric anisotropy Compound(s) ($\|\Delta\epsilon\|<3$) | One or more compounds of Formula (I) optionally together with one or more compounds selected from Formulae (Va) to (Vk). | 5–90% preferably 20–50% |
| Component 4: chiral compound(s) | One or more chiral compounds. | 0–2% |

The compound(s) of Formula (I) preferably constitute from 5 to 30% by weight of the overall material composition.

In the material whose composition is defined by Table 1 the compound(s) of Formula (I) not only help to reduce the viscosity and extend the temperature range of the nematic liquid crystal phase of the mixture at the lower end but also help to improve the multiplexibility of the mixture.

Liquid crystal mixtures including compounds of Formula (I) may be formed in a known way, eg simply by heating the constituent compounds to form an overall isotropic liquid, stirring the liquid for a short period, eg about 10 minutes, and allowing it to cool.

To provide more general examples of a mixture according to the second aspect at least one compound according to Formula (I) above may be mixed together with one or more compounds in any one or more of the following known families for use in one or more of the applications given above (the actual application(s) depending on the mixture's properties):

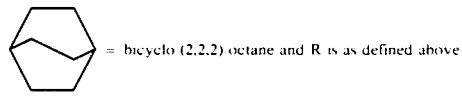
i

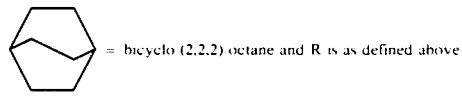
ii

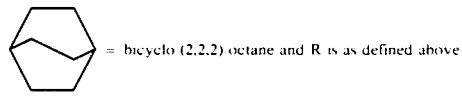
iii

-continued
| | |
|---|---|
| 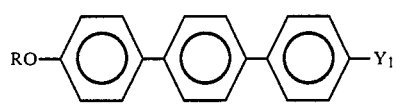 | iv |
| 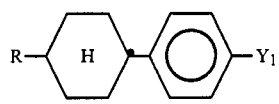 | v |
| 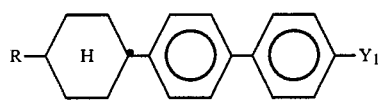 | vi |
| 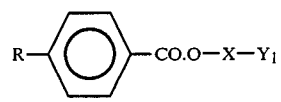 | vii |
| 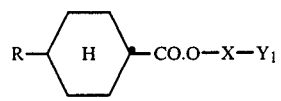 | viii |
| 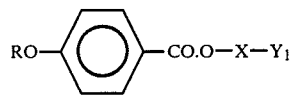 | ix |
| 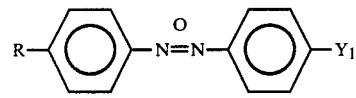 | x |
| 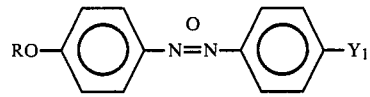 | xi |
| 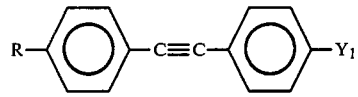 | xii |
| 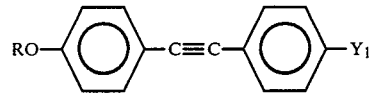 | xiii |
| 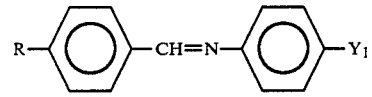 | xiv |
| 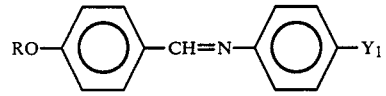 | xv |
|  | xvi |
-continued
| | |
|---|---|
| 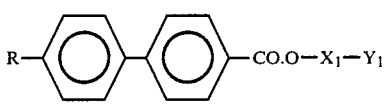 | xvii |
| 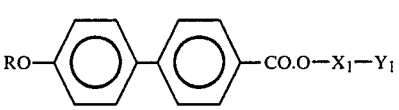 | xviii |
| 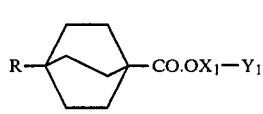 | xix |
| 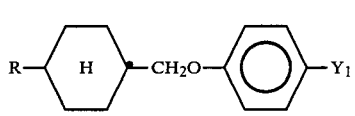 | xx |
| 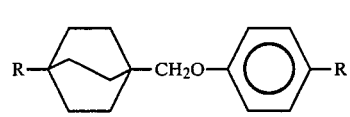 | xxi |
| 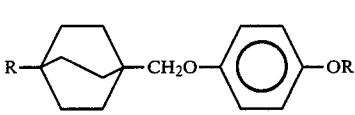 | xxii |
| 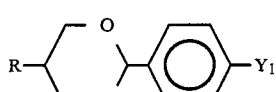 | xxiii |
| 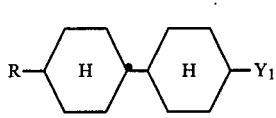 | xxiv |
| 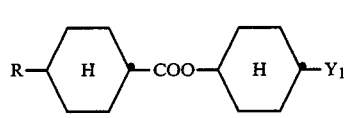 | xxv |
| 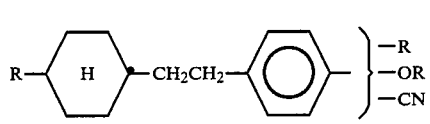 | xxvi |
| 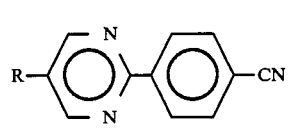 | xxvii |
where
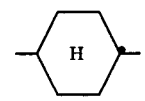
is a trans-1,4-disubstituted cyclohexane ring,

is a 1,4-disubstituted bicyclo(2,2,2)octane ring, X is a 1,4 phenylene group

a 4,4'-biphenylyl group

a 2,6-naphthyl group

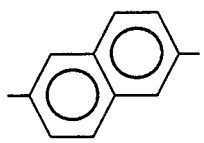

or a trans-1,4-disubstituted cyclohexane ring, and $Y_1$ is CN, or R' or CO.O—X—$Y^1$ where $Y^1$ is CN, or R' or OR'; where R and R' are alkyl groups; or a derivative of one of these wherein H is replaced by a halogen, eg F, in one of the benzene rings.

Preferably, the compound(s) of Formula (I) comprises between 5 and 30% by weight of the mixture.

According to the present invention in a second aspect a liquid crystal device includes two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterised in that the liquid crystal material consists of or includes a compound according to Formula (I) above.

The device according to the second aspect may be a twisted nematic effect device, which may or may not be operated in a multiplexed fashion, a cholesteric-to-nematic phase change effect device, a Fréedericksz effect device or a two-frequency switching effect device, all constructed in a known manner or any of the other devices mentioned above. The various ways in which compounds according to Formula I may be used in these devices are outlined above and will be further apparent to those skilled in the art.

DESCRIPTION OF THE PREFERRED EMBODIMENTS

Examples of the preparation and properties of compounds of Formula I will not be given.

The following abbreviations are used in the Examples.
Ms = mass spectrum
NMR = nuclear magnetic resonance spectrum
IR = infrared absorption spectrum
$\nu_{max}$ = infrared absorption peak
δ = chemical shift (ppm) from denteriochloroform ($CDCl_3$ solution)
s = singlet
t = triplet
m = multiplet
ppm = parts per million
glc = gas-liquid chromatography
THF = tetrahydrofuran

EXAMPLE 1

The preparation of 1,4-di-n-pentylbicyclo(2,2,2)octane by route 1 given above.

Step A1: Preparation of 1-pentanoyl-4-n-pentylbicyclo(2,2,2)octane

1-Bromobutane (10.45 g, 0.076 mol) in dry benzene (9 ml) was added dropwise to magnesium (1.68 g, 0.069 mol) in dry benzene (3 ml) and dry THF (9.98 g) during 75 min. The reaction mixture was stirred at room temperature for 1 h. Triethylamine (28.84 g, 0.285 mol) was added at 5°–10° C. and methyl 4-n-pentylbicyclo(2,2,-2)octane-1-carboxylate (3.00 g, 0.013 mol) in dry benzene (27 ml) was added dropwise during 1 h at 5°–15° C. The ice bath was removed and the reaction mixture was left stirring at room temperature for 4 h, and the progress of the reaction was followed by glc until the ester peak had almost disappeared. The reaction mixture was diluted with water and the organic layer was washed with 4N-hydrochloric acid (3×50 ml). The aqueous layer was washed with ether (3×50 ml) and the ether layers were combined with the organic layer and washed with water (3×50 ml) and dried ($MgSO_4$). The ether was removed and the residue dried in vacuo and used directly to make the required compound.

The crude yield was 3.01 g, 88%

The product was confirmed by measuring the following infrared absorption peaks ($\nu_{max}$) for a film specimen:
$\nu_{max}(cm^{-1})$ 2925, 2860, 1700 (C=O), 1455, 1380

Step B1: Preparation of 1,4-di-n-pentylbicyclo(2,2,2)octane

A mixture of 1-pentanoyl-4-n-pentylbicyclo(2,2,2)octane (3.00 g, 0.01 mol), hydrazine hydrate (18 ml, 100%) and potassium hydroxide (5.00 g) in diethylene glycol (50 ml) was stirred and heated under reflux for 5 h (170° C., oil bath temperature). The mixture was cooled and potassium hydroxide (2.00 g) and hydrazine hydrate (3 ml, 100%) were added and the apparatus was arranged for distillation. The oil bath temperature was raised slowly to 250° C. during 2 h and maintained at this temperature for 2 h. The reaction mixture and the distillate were cooled separately, diluted with water and washed with ether (3×50 ml). The ether layers were combined, washed with water (2×50 ml) and then dried ($MgSO_4$). The ether was removed and the residue was chromatographed on a neutral alumina column (Brockmann activity = 1; 30 cm × 1 cm) using light petroleum (bp 40°–60° C.). Four fractions (15 ml each) were collected and analysed by glc. The solvent was removed and the residue was distilled to give the required di-alkyl compound.

The boiling point of the product was 120°–140° C./0.5 mm Hg.

The yield was 1.83 g, 65%.

The product showed the following $^{13}C$ NMR spectroscopic results:

| δ ppm | integration |
|---|---|
| 14.08 | 1611 |
| 22.75 | 2971 |
| 23.40 | 3046 |
| 30.61 | 1706 |
| 31.48 | 7388 |
| 32.99 | 2837 |
| 42.88 | 2702 |

The product was confirmed by measuring the following IR $\nu_{max}$.

IR $\nu_{max}$ (film): 2930, 2860, 1455, 1380 cm$^{-1}$ and the following mass spectral (Ms) data:
Ms: M$^+$250

EXAMPLE 2

1-n-Pentyl-4-n-propylbicyclo(2,2,2)octane was prepared by a procedure analogous to that of Example 1. This product was obtained in a yield of 38% and had a boiling point of 158°-162° C. (15 mm Hg). The product was confirmed by $^1$H NMR, IR and Ms measurements.

EXAMPLE 3

1-n-Heptyl-4-n-pentylbicyclo(2,2,2)octane was prepared by a procedure analogous to that of Example 1. This product had a boiling point of 120°-124° C. (0.15 mm Hg) and was obtained in a yield of 45%. The product was confirmed by $^1$H NMR, IR and Ms measurements.

EXAMPLE 4

1-Ethyl-4-n-propyl-bicyclo(2,2,2)octane was prepared by a procedure analogous to that of Example 1. This product had a boiling point of 84°-98° C. (15 mm Hg) and was obtained in a yield of 30%. This product was confirmed by 1$^H$ NMR, IR and Ms measurements.

The following compounds listed in Table 2 may also be prepared analogously to the procedure of Example 1:

TABLE 2

Compounds of formula

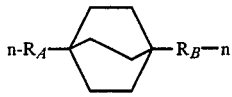

n-R$_A$— —R$_B$—n

| R$_A$ | R$_B$ | R$_A$ | R$_B$ |
|---|---|---|---|
| C$_3$H$_7$ | C$_3$H$_7$ | C$_4$H$_9$ | C$_8$H$_{17}$ |
| C$_3$H$_7$ | C$_4$H$_9$ | C$_5$H$_{11}$ | C$_6$H$_{13}$ |
| C$_3$H$_7$ | C$_6$H$_{13}$ | C$_5$H$_{11}$ | C$_8$H$_{17}$ |
| C$_3$H$_7$ | C$_7$H$_{15}$ | C$_6$H$_{13}$ | C$_6$H$_{13}$ |
| C$_3$H$_7$ | C$_8$H$_{17}$ | C$_6$H$_{13}$ | C$_7$H$_{15}$ |
| C$_4$H$_9$ | C$_4$H$_9$ | C$_6$H$_{13}$ | C$_8$H$_{17}$ |
| C$_4$H$_9$ | C$_5$H$_{11}$ | C$_7$H$_{15}$ | C$_7$H$_{15}$ |
| C$_4$H$_9$ | C$_6$H$_{13}$ | C$_7$H$_{15}$ | C$_8$H$_{17}$ |
| C$_4$H$_9$ | C$_7$H$_{15}$ | C$_8$H$_{17}$ | C$_8$H$_{17}$ |

EXAMPLE 5

Preparation of 1-methyl-4-n-pentylbicyclo(2,2,2)octane by route 2 given above.

A mixture of 1-chloromethyl-4-n-pentylbicyclo(2,2,-2)octane (1.34 g, 0.006 mol) and t-butanol (2.39 g. 0.032 mol) was added to finely cut lithium metal (0.55 g, 0.08 g atom) in dry THF (34 ml). The reaction mixture was left stirring at room temperature for 2 h. The temperature was raised to 65° C. and the reaction mixture was left stirring at this temperature for 5 h, then it was cooled and diluted with water (100 ml) and washed with ether (3×70 ml). The ether solution was washed with water (4×30 ml) and dried (MgSO$_4$). The solvent was removed and the residue was distilled in a short path distillation apparatus under reduced pressure to give the required compound.

The boiling point of the product was 100°-110° C. (15 mm Hg).

The yield was 0.89 g, 64%.

The product showed the following $^1$H NMR results:
$^1$H NMR; δ: 0.75 (s, 3H), 0.90 (t, 3H), 1.15 (m, 8H), 1.33 (s, 12H)

The product also showed the following $\nu_{max}$ $\nu_{max}$ (film) 2930, 2850, 1455, 1375 cm$^{-1}$.

The product also showed the following Ms data:
Ms; M$^+$ = 194.

EXAMPLE 6

The preparation of 1-n-butoxy-4-n-propylbicyclo(2,2,2)octane prepared by Route 3 given above.

Step A3: Preparation of 4-n-butoxy-1-n-propylbicyclo(2,2,2)octane-2-one

A mixture of 4-acetyl-4-n-propylcyclohexanone (3.65 g, 0.02 mol), tri-butylorthoformate (13.91 g, 0.06 mol) and toluene-p-sulphonic acid monohydrate (0.30 g) in Analak (Trade Mark) butan-1-ol (25 ml) was stirred at room temperature for 60 h. The progress of the reaction was followed by glc. The reaction mixture was diluted with ether (200 ml), washed with aqueous sodium carbonate (2×50 ml, 10%) and with water (2×50 ml) and the ether layer was dried (MgSO$_4$). Ether was removed and the residue was chromatographed on a neutral alumina column (1.5×30 cm) using light petroleum (bp, 40°-60° C.) as eluent. Five fractions were collected (20 ml each) and combined. The solvent was removed and the residue was distilled in a short-path distillation apparatus to give the required compound.

The boiling point of the product of Step A3 was 105°-115° C. (0.15 mm Hg).

The yield was 3.72 g, 78%.

The following $^1$H NMR, IR, and Ms data were measured for the product:
$^1$H NMR; δ:0.90 (t, 6H), 1.32 (m, 8H), 1.70 (s, 8H) 2.38 (s, 2H), 3.34 (t, 2H) ppm.

IR (film): $\nu_{max}$ 2960, 2870, 1725 (C=O), 1460, 1335, 1115 (C-O) cm$^{-1}$.

Ms; M$^+$ =238.

Step B3: The preparation of 1-n-butoxy-4-n-propylbicyclo(2,2,2)octane

A mixture of 4-n-butoxy-1-n-propylbicyclo(2,2,2)octane-2-one (2.08 g, 0.009 mol) hydrazine hydrate (8.4 ml, 98-100%) and potassium hydroxide (2.80 g, 0.050 mol) in diethylene glycol (40 mol) was stirred and heated under reflux for 4 h (180° C., oil bath temperature). The reaction mixture was cooled and hydrazine hydrate (4 ml) and potassium hydroxide (1.00 g) were added and the apparatus was arranged for distillation. The temperature was raised slowly to 240° C. in 2 h, and the reaction mixture was kept at this temperature for 2 h. The reaction mixture was cooled and the residue and the distillate were separately diluted with water, washed with ether (3×50 ml). All the ether washings were combined and washed with water (2×50 ml) dilute hydrochloric acid (2×50 ml) and water (2×50 ml).

The ether solution was dried (MgSO₄) and ether was removed to give a residue which was chromatographed on a neutral alumina column (1.5×30 cm) using light petroleum (bp 40°-60° C.) as eluent. Four fractions were collected (20 ml each) the solvent was removed to leave a residue which was distilled in a short-path distillation apparatus under reduced pressure to give the required compound.

The boiling point of the product was 142°-146° C. (15 mm Hg).

The yield was 1.02 g, 53%.

The following ¹H NMR, IR and Ms data were measured for the product:

¹H NMR: δ:0.90 (t, 6H), 1.08 (m, 8H), 1.54 (s, 12H), 3.28 (t, 2H), ppm.

IR (film): $\nu_{max}$: 2950, 2860, 1455, 1355, 1140, 1105 (C-O) cm⁻¹.

Ms: M⁺ = 224.

EXAMPLE 7

1-n-Butoxy-4-n-pentylbicyclo(2,2,2)octane was prepared by a procedure analogous to that of Example 6.

This product, which had a boiling point of 178°-182° C. (15 mm Hg) was obtained in a yield of 40%.

The following ¹H NMR, IR and Ms data were measured for the product:

¹H NMR: δ:0.90 (t, 6H), 1.12 (m, 12H), 1.56 (s, 12H), 3.28 (t, 2H) ppm

IR (film): $\nu_{max}$ 2950, 2860, 1455, 1335, 1140, 1105 (C-O) cm⁻¹

Ms: M⁺ = 252.

EXAMPLE 8

1-n-Butoxy-4-n-heptylbicyclo(2,2,2)octane was prepared by a procedure analogous to that of Example 6.

This product, which had a boiling point of 125°-130° C. (0.2 mm Hg) was obtained in a yield of 60%.

The following ¹H NMR, IR and Ms data were measured for the product:

¹H NMR: δ:0.90 (t, 6H), 1.28 (m, 16H), 1.56 (s, 12H), 3.32 (t, 2H) ppm

IR (film): $\nu_{max}$: 2940, 2860, 1455, 1355, 1140, 1105 (C-O) cm⁻¹.

Ms: M⁺ = 280.

EXAMPLE 9

1-Ethoxy-4-n-propylbicyclo(2,2,2)octane was prepared by a procedure analogous to that of Example 6.

This product, which was obtained in a yield of 47% had a boiling point of 118°-124° C. (15 mm Hg).

The following ¹H NMR, IR and Ms data were measured for the product.

¹H NMR: δ:0.90 (t, 6H), 1.16 (m, 4H), 1.60 (s, 12H), 3.60 (q, 2H) ppm

IR (film): $\nu_{max}$: 2955, 2870, 1455, 1335, 1140, 1110 (C-O) cm⁻¹

Ms: M⁺ = 196.

The following additional compounds listed in Table 3 may also be prepared by a procedure analogous to that of Example 6.

TABLE 3

Compounds of Formula n-R$_C$—⟨bicyclooctane⟩—OR$_D$—n

| R$_C$ | R$_D$ | R$_C$ | R$_D$ | R$_C$ | R$_D$ |
|---|---|---|---|---|---|
| C₃H₇ | C₃H₇ | C₅H₁₁ | C₂H₅ | C₇H₁₅ | C₂H₅ |
| C₃H₇ | C₅H₁₁ | C₅H₁₁ | C₅H₁₁ | C₇H₁₅ | C₃H₇ |
| C₃H₇ | C₆H₁₃ | C₅H₁₁ | C₆H₁₃ | C₇H₁₅ | C₆H₁₃ |
| C₃H₇ | C₂H₅ | C₅H₁₁ | C₇H₁₅ | C₇H₁₅ | C₇H₁₅ |
| C₃H₇ | C₈H₁₇ | C₅H₁₁ | C₈H₁₇ | C₇H₁₅ | C₈H₁₇ |
| C₄H₉ | C₂H₅ | C₆H₁₃ | C₂H₅ | C₈H₁₇ | C₂H₅ |
| C₄H₉ | C₄H₉ | C₆H₁₃ | C₃H₇ | C₈H₁₇ | C₃H₇ |
| C₄H₉ | C₅H₁₁ | C₆H₁₃ | C₅H₁₁ | C₈H₁₇ | C₅H₁₁ |
| C₄H₉ | C₆H₁₃ | C₆H₁₃ | C₆H₁₃ | C₈H₁₇ | C₆H₁₃ |
| C₄H₉ | C₇H₁₅ | C₆H₁₃ | C₇H₁₅ | C₈H₁₇ | C₇H₁₅ |
| C₄H₉ | C₈H₁₇ | C₆H₁₃ | C₈H₁₇ | C₈H₁₇ | C₈H₁₇ |

EXAMPLE 10

The preparation of 1-n-Pentylbicyclo(2,2,2)octane by Route 4 given above.

Lithium metal in small pieces (0.6865 g, 0.1 g.at.) was added to a mixture of 1-bromo-4-pentylbicyclo(2,2,-2)octane (2.6043 g, 0.01 mol) in dry THF (75 ml). The reaction mixture was stirred and warmed at 60° C. for 4 h and the progress of the reaction was followed by glc. The reaction mixture was then cooled, the lithium metal was filtered off and the filtrate was diluted with water (180 ml) and washed with ether (3×70 ml). The ether layers were combined and washed with water (3×10 ml) dried (MgSO₄) and the ether was removed to give a residue which was distilled in a short-path distillation apparatus under reduced pressure (water pump) to give the required compound.

The following measurements were made for this product:

Boiling Point: 100°-110° C./15 mm Hg

Yield: 1.6805 g, 93%.

¹H NMR: δ:0.90 (t, 3H), 1.10 (m, 9H), 1.33 (s, 6H), 1.35(s, 6H) ppm

IR: $\nu_{max}$ (film) 2930, 2870, 1460 cm⁻¹

Ms: M⁺ = 180.

The following properties listed in Table 4 have also been measured for compounds of Formula I:

(i) Clearing point (denoted as T$_{N-I}$) of the compound which was obtained by extrapolation from the clearing point results obtained using 10% and 25% by weight mixtures of the compound in the known material ZLI 1132 obtained from E Merck Co.

(ii) "Nematic" viscosity (denoted as η₂₀° or η₀°) of the compound obtained by extrapolation of the viscosity results obtained using a 20% weight mixture of the compound in ZLI 1132 at 20° C. and 0° C. respectively:

TABLE 4

Properties of compounds of Formula:

R₁—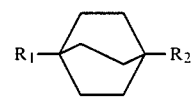—R₂

| Compound | | | | |
|---|---|---|---|---|
| R₁ | R₂ | T$_{N-I}$(°C.) | η₂₀°(cps) | η₀°(cps) |
| n-C₃H₇ | C₂H₅ | −147 to −142 | 5.0 | 3.5 |
| n-C₅H₁₁ | n-C₅H₁₁ | −36 to −30 | 7.7 | 20.2 |

TABLE 4-continued

Properties of compounds of Formula:

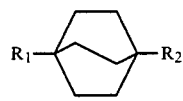

| Compound | | | | |
|---|---|---|---|---|
| $R_1$ | $R_2$ | $T_{N-I}(°C.)$ | $\eta_{20°}(cps)$ | $\eta_{0°}(cps)$ |
| n-$C_5H_{11}$ | n-$C_4H_9O$ | −92 to −88 | 14.4 | 21.7 |
| n-$C_3H_7$ | n-$C_4H_9O$ | −115 to −111 | — | — |
| n-$C_7H_{15}$ | n-$C_4H_9O$ | −85 to −82 | — | — |
| n-$C_5H_{11}$ | n-$CH_3$ | −136 to −125 | 9.7 | 12.0 |
| n-$C_5H_{11}$ | n-$C_3H_7$ | −77 to −72 | 6.6 | 4.5 |
| n-$C_5H_{11}$ | n-$C_7H_{15}$ | −30 to −24 | 8.4 | 22.2 |
| n-$C_5H_{11}$ | H | −107 to −96 | 51.4 | 29.13 |

The compounds 1-n-pentyl-4-n-propylbicyclo(2,2,-2)octane, compound $X_1$, 1,4-di-n-pentyl-bicyclo(2,2,-2)octane, compound $X_2$, and 1-n-heptyl-4-n-pentylbicyclo(2,2,2)octane compound $X_3$ were further investigated in comparison with the low viscosity compound of formula

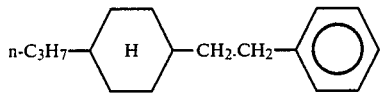

(trans-isomer), compound Y, as follows. Each additive compound ie compound $X_1$, $X_2$, $X_3$ and Y was added in turn to Mixture A defined as follows, the additive compound forming in each case 27% by weight of the overall mixture. The clearing point $T_{N-I}(°C.)$ and viscosity at various temperatures was measured for each overall mixture formed.

The Mixture A used was as defined in Table 5: (for each

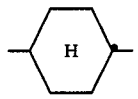

the trans isomer is used)

TABLE 5

| Mixture A | |
|---|---|
| Compound | Parts by weight |
| n-$C_3H_7$—⟨H⟩—⟨○⟩—CN | 10 |
| n-$C_5H_{11}$—⟨H⟩—⟨○⟩—CN | 5 |
| n-$C_3H_7$—⟨H⟩—⟨○⟩—$OC_2H_5$ | 10 |
| n-$C_5H_{11}$—⟨H⟩—⟨○⟩—⟨○⟩—CN | 7 |
| n-$C_5H_{11}$—⟨H⟩—⟨○⟩—⟨○⟩—$C_2H_5$ | 17 |

TABLE 5-continued

| Mixture A | |
|---|---|
| Compound | Parts by weight |
| n-$C_5H_{11}$—⟨H⟩—⟨○⟩—⟨○⟩—⟨H⟩—$C_3H_7$—n | 10 |
| n-$C_3H_7$—⟨H⟩—⟨○⟩—CO.O—⟨○⟩—$C_3H_7$—n | 8 |
| n-$C_5H_{11}$—⟨H⟩—⟨○⟩—CO.O—⟨○⟩—$C_3H_7$—n | 6 |

The results obtained for the overall mixtures are as shown in Table 6 as follows wherein Y, $X_1$, $X_2$ and $X_3$ have the following formulae:

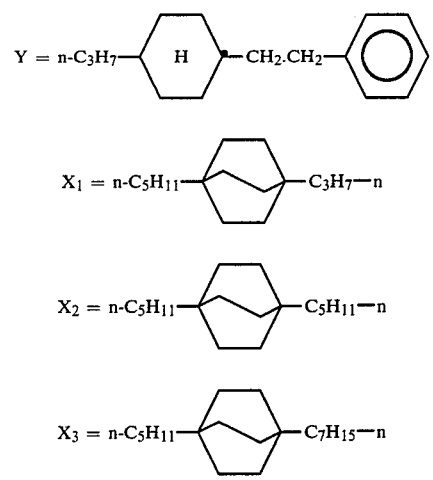

TABLE 6

| Comparative properties of Mixture A together with various low viscosity additives | | | | |
|---|---|---|---|---|
| Compound No. added | Y | $X_1$ | $X_2$ | $X_3$ |
| Viscosity at 20° C. (cps) | 22 | 21.0 | 22.1 | 24 |
| Viscosity at 10° C. (cps) | 36 | 35.0 | 36.8 | 39.6 |
| Viscosity at 0° C. | 64 | 63 | 68 | 71.5 |
| Viscosity at −10° C. | 135 | 136 | 145 | 152 |
| Viscosity at −14° C. | — | 192.4 | 226 | — |
| $T_{N-I}(°C.)$ | 72 | 79 | 86 | 81.8 |

Table 6 demonstrates that compounds $X_1$, $X_2$ and $X_3$ show mixture viscosities similar to those shown by compound Y but, beneficially, compounds $X_1$, $X_2$, $X_3$ show a mixture $T_{N-I}$ depression not as great as that shown by compound Y.

The display of FIGS. 1 to 4 comprises a cell 1, formed of two, front and back, glass slides 2, 3 respectively, spaced about 7 μm apart by a spacer 4 all held together by an epoxy resin glue. A liquid crystal material 12 fills the gap between the slides 2, 3 and the spacer 4. In front of the front glass slide 2 is a front polariser 5 arranged with its axis of polarisation axis horizontal. A reflector 7 is arranged behind the slide 3. A rear polariser 6 or analyser is arranged between the slide 3 and reflector 7.

Figure 3:
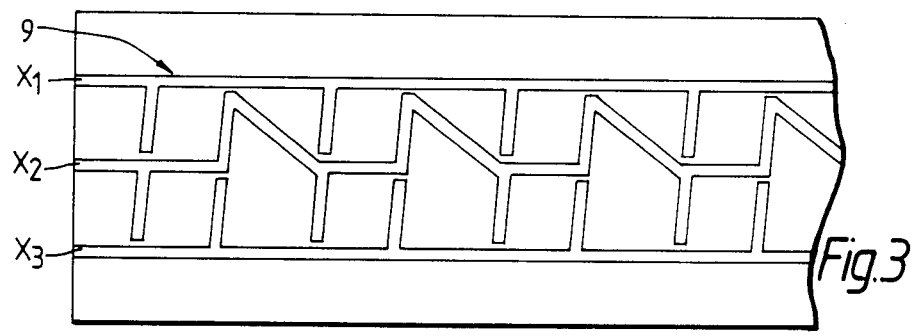
FIG. 3 shows a rear electrode configuration for FIG. 1.
Figure 4:
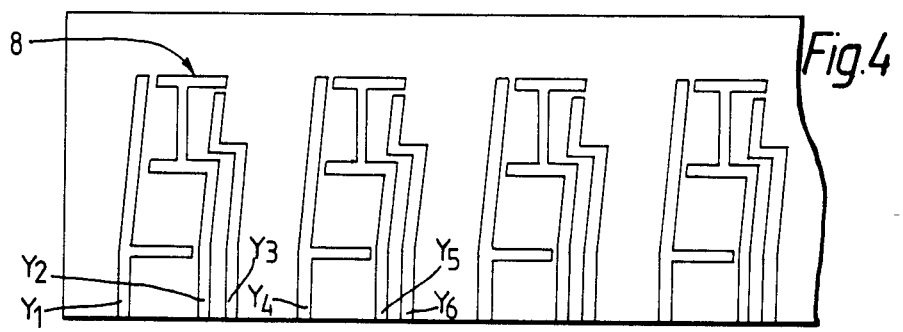
FIG. 4 shows a front electrode configuration for FIG. 1.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 3 the rear electrode structure is formed into three electrodes $x_1$, $x_2$, $x_3$. Similarly the front electrode structure is formed into three electrodes per digit and decimal point $y_1$, $y_2$, $y_3$.... Examination of the six electrodes per digit shows that each of the eight elements can independently have a voltage applied thereto by application of suitable voltage to appropriate x, y electrodes.

Prior to assembly the slides 2, 3 bearing the electrodes are cleaned then dipped in a solution of 0.2% by weight of poly-vinyl alcohol (PVA) in water. When dry, the slides are rubbed in a single direction with a soft tissue then assembled with the rubbing directions orthogonal to one another and parallel to the optical axis of the respective adjacent polarisers, ie so that the polarisers are crossed. When the nematic liquid crystal material 12 is introduced between the slides 2, 3 the molecules at the slide surfaces lie along the respective rubbing directions with a progressive twist between the slides.

When zero voltage is applied to the cell 1 light passes through the front polariser 5, through the cell 1 (whilst having its plane of polarisation rotated 90°) through its rear polariser 6 to the reflector 7 where it is reflected back again to an observer (shown in FIG. 1 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2,3, ie along the axis Z. Thus light at the position does not reach the reflector 7 and does not reflect back to the observer who sees a dark display of one or more bars of a digit 10.

Figure 5:
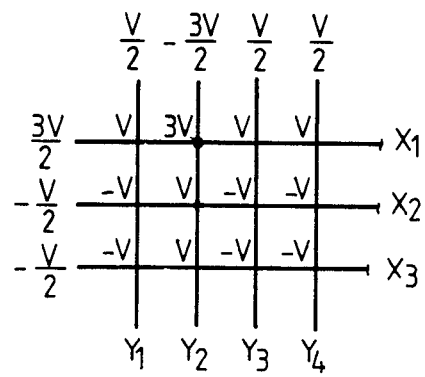
FIGS. 5, 6 and 7 show schematic views of the device of FIGS. 1-4 with typical addressing voltages.
Figure 6:
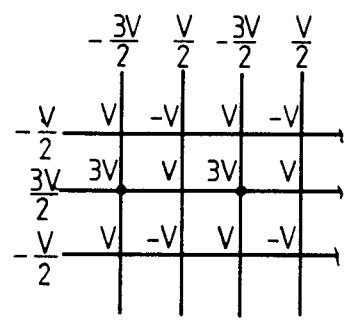
Figure 7:
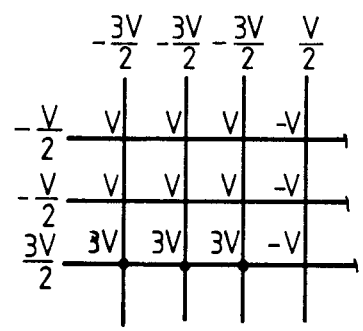

Voltages are applied as follows as shown in FIGS. 5, 6 and 7 for three successive time intervals in a linescan fashion. An electrical potential of 3 V/2 is applied to, ie scanned down, each x electrode in turn whilst $-V/2$ is applied to the remaining x electrodes. Meanwhile $-3$ V/2 or V/2 is applied to the y electrodes. A coincidence of 3 V/2 and $-3$ V/2 at an intersection results in a voltage 3 V across the liquid crystal layer 12. Elsewhere the voltage is V or $-V$. Thus by applying $-3$ V/2 to appropriate y electrodes as 3 V/2 is scanned down the x electrodes selected intersections are turned ON as indicated by solid circles. The electric voltage V is an ac signal of eg 100 Hz square wave, and the sign indicates the phase.

It will be apparent to those skilled in the art that the device shown in FIGS. 1 to 7 is a multiplexed display because the electrodes are shared between ON and OFF intersections or display elements.

A material embodying the second aspect of the invention which is suitable for use as the material 12 in the above device is Mixture A (73% by weight) together with 27% by weight of Compound X₁ defined above.

Small amounts of a cholesteric material may be added to the nematic material to induce a preferred twist in the molecules in the liquid crystal layer. This and the use of appropriate slide surface treatment removes the problems of display patchiness as taught in UK Patent Ser. Nos. 1,472,247 and 1,478,592.

Suitable cholesteric materials are:

C15: about 0.1-0.5% by weight and CB15: about 0.01% to 0.05% by weight.

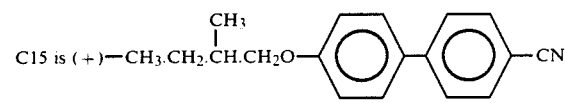

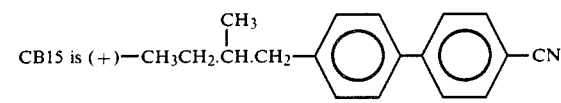

Small amounts of pleochroic dye may be added to enhance the display contrast, eg one of the anthroquinone dyes described in UK Patent Specification No. 2011940A. One polariser is removed in this case.

In another embodiment mixtures embodying the second aspect of the invention may be used in a Fréedericksz effect cell. Such a cell may be constructed by sandwiching the liquid crystal material between glass slides having electrode films deposited on their inner surfaces as in the above device. However, in this case the polarisers are not necessary; the glass slide inner surfaces are treated with a coating of lecithin and the liquid crystal material is a negative material whose molecules are aligned in the OFF state perpendicular to the slide substrates (homeotropic texture) by the lecithin coating. Application of an appropriate electric field across the material in the ON state re-arranges the molecules parallel to the slide surfaces (homogeneous texture). A pleochroic dye may be incorporated in the liquid crystal material to enhance the contrast between the ON and OFF states.

A Freedericksz effect cell made in the above way may incorporate Mixture 3 below, the cell spacing being 10 μm.

TABLE 7

Mixture 3

| Compound | Weight Percentage |
|---|---|
| 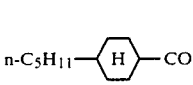 | 30 |
| 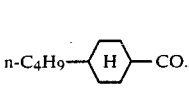 | 30 |
| 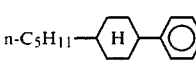 | 20 |
| 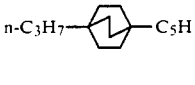 | 20 |
| Compound A = 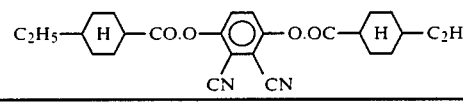 | | may optionally be added to Mixture 3 (up to 3% by weight of Mixture 3) as a negative additive.

The preparation of Compound A is described in published UK patent application No. 2061256A. About 1% by weight of a known pleochroic dye eg 1,5-bis-4'-n-butylphenylaminoanthraquinone may be added to Mixture 3 to give a dyed mixture. (Mixture 3A)

When a voltage is applied across the cell, the colour changes from a weakly absorbing state to a strongly absorbing state.

In an alternative embodiment of the invention a (cholesteric-to-nematic) phase change effect device incorporates a material as defined above.

A cell is prepared containing a long helical pitch cholesteric material sandwiched between electrode-bearing glass slides as in the twisted nematic cell described above. However the polarisers and surface preparations for homogeneous alignment, eg treatment of the glass slide surfaces with SiO, are not used in this case.

If the glass slides are untreated and the liquid crystal material has a positive dielectric anisotropy ($\Delta\epsilon$) the liquid crystal material is in a twisted focal conic molecular texture in the OFF state which scatters light. The effect of an electric field applied between a pair of electrodes on the respective inner surface of the glass slides is to convert the region of liquid crystal material between the electrodes into the ON state which is a homeotropic nematic texture which is less scattering than the OFF state. This is a 'negative contrast' type of phase change effect device.

If the inner glass slide surfaces are treated, eg with a coating of lecithin, to give alignment perpendicular to those surfaces, and the liquid crystal material has $\Delta\epsilon$ negative the material in the OFF state is in a homeotropic texture which has little scattering effect on incident light. If an electric field is applied between a pair of electrodes on the respective inner surfaces of the glass slides the region of liquid crystal material between the electrodes is converted to a twisted homogeneous texture which scatters light (the ON state). This is a 'positive contrast' type of phase change effect device.

The contrast between the two states in each case may be enhanced by the addition of a small amount of a suitable pleochroic dye (eg 1% by weight of 1,5-bis-4'-n-butylphenylaminoanthraquinone in the case where $\Delta\epsilon$ is positive) to the liquid crystal material.

A suitable positive dielectric anisotropy material, Mixture 4, embodying the invention for use in a phase change effect (negative contrast type) device is:

TABLE 8

| Component | Mixture 4 Weight Percentage |
|---|---|
| Mixture A (defined above) | 70 |
| 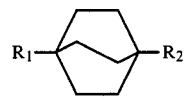 n-C$_5$H$_{11}$—()—C$_7$H$_{15}$—n | 25 |
| 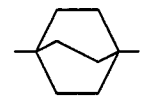 R$_c$—()—()—CN | 5 |

(R$_c$ = (+)-2-methylbutyl)

A suitable negative dielectric anistropy material embodying the invention for use in a phase change effect (positive contrast type) device, Mixture 5, is as follows:

TABLE 9

| Material | Mixture 5 Weight Percentage |
|---|---|
| Mixture 3 | 99 |

TABLE 9-continued

| Material | Mixture 5 Weight Percentage |
|---|---|
| 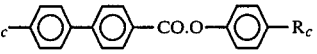 R$_c$—()—()—CO.O—()—R$_c$ | 1 |

(R$_c$ = (+)-2-methylbutyl)

Examples of high birefringence, low viscosity materials of positive dielectric anisotropy suitable for simple twisted nematic displays and which include a compound of Formula (I) are Mixtures 6 and 7 defined in Tables 12 and 13 as follows:

We claim:

1. A liquid crystal composition which comprises a mixture of compounds and which includes at least one additive compound of Formula I as follows:

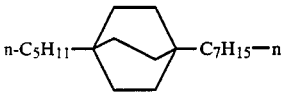

wherein R$_1$ represents an alkyl group, R$_2$ represents an alkyl or alkoxy group or hydrogen and

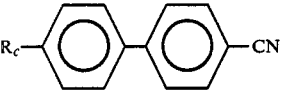

represents a 1,4-disubstituted bicyclo(2,2,2)octane ring.

2. A composition as claimed in claim 1 wherein in Formula I R$_1$ is n-alkyl, R$_2$ is n-alkyl or n-alkoxy and each of R$_1$ and R$_2$ independently has from 1 to 12 carbon atoms.

3. A composition as claimed in claim 2 wherein each of R$_1$ and R$_2$ independently has from 1 to 8 carbon atoms.

4. A composition as claimed in claim 1 wherein the composition comprises a host material including one or more liquid crystal compounds which melt at less than 80° C., the composition exhibiting a nematic or chiral nematic liquid crystal phase at 20° C.

5. A composition as claimed in claim 1 wherein the at least one compound of Formula I forms between 2% and 50% by weight of the composition.

6. A composition as claimed in claim 5 wherein the at least one compound of Formula I forms between 5% and 30% by weight of the composition.

7. A composition as claimed in claim 1 which comprises:
Component 1: one or more compounds having a melting point less than 80° C. and a positive dielectric anisotropy, the compound or compounds showing a nematic phase at 20° C.;
Component 2: one or more nematic compounds having a clearing point greater than 100° C.;
Component 3: one or more compounds showing a dielectric anisotropy magnitude less than 3 and including one or more compounds of Formula I; and
Component 4: one or more chiral compounds;
the components being in the following proportions by weight:
Component 1: 30% to 70%
Component 2: 10% to 30%
Component 3: 20% to 50%
Component 4: 0% to 2%
provided the sum of the weight percentages of Components 1 to 4 totals 100%.

* * * * *